(12) United States Patent
Oakes (10) Patent No.: US 9,474,643 B2
(45) Date of Patent: Oct. 25, 2016

(54) PUMPS

(75) Inventor: John Oakes, Yorkshire (GB)

(73) Assignee: Ultramax Products Limited, West Yorkshire (GB)

( * ) Notice: Subject to any disclaimer, the term of this patent is extended or adjusted under 35 U.S.C. 154(b) by 794 days.

(21) Appl. No.: 13/883,454

(22) PCT Filed: Apr. 28, 2011

(86) PCT No.: PCT/GB2011/050848
§ 371 (c)(1),
(2), (4) Date: Aug. 13, 2013

(87) PCT Pub. No.: WO2011/135374
PCT Pub. Date: Nov. 3, 2011

(65) Prior Publication Data
US 2013/0317289 A1    Nov. 28, 2013

(30) Foreign Application Priority Data

Apr. 30, 2010 (GB) .................................. 1007292.4
Jan. 28, 2011 (GB) .................................. 1101481.8

(51) Int. Cl.
*A61F 5/41* (2006.01)

(52) U.S. Cl.
CPC ............ *A61F 5/41* (2013.01); *A61F 2005/412* (2013.01)

(58) Field of Classification Search
CPC ............... A61F 5/41; A61F 2005/412; A61B 10/0058; A61B 10/00; A61H 19/32

USPC ....................................................... 600/38–41
See application file for complete search history.

(56) References Cited

U.S. PATENT DOCUMENTS

| | | | |
|---|---|---|---|
| 5,669,869 A * | 9/1997 | Strom | ............................. 600/38 |
| 5,997,470 A | 12/1999 | Coates | |
| 2005/0033113 A1 | 2/2005 | Bonthuys | |
| 2005/0119521 A1 * | 6/2005 | Pitcher | ........................... 600/38 |
| 2007/0156014 A1 | 7/2007 | Zafirakis | |
| 2008/0269554 A1 * | 10/2008 | Oakes | ............................. 600/39 |

FOREIGN PATENT DOCUMENTS

| | | |
|---|---|---|
| DE | 42 18 294 C1 | 5/1993 |
| DE | 43 44 686 A1 | 6/1995 |
| GB | 2 417 686 A | 3/2006 |
| WO | WO-2006/024874 A2 | 3/2006 |

OTHER PUBLICATIONS

International Search Report issued in International Application No. PCT/GB2011/050848 dated Oct. 14, 2011.
International Preliminary Report on Patentability issued in International Application No. PCT/GB2011/050848 dated Nov. 6, 2012.

* cited by examiner

*Primary Examiner* — Samuel Gilbert
(74) *Attorney, Agent, or Firm* — Venable LLP; Michael A. Sartori; Steven J. Schwarz (57) ABSTRACT

A pump (102) comprising a chamber (108) adapted to receive a penis, a non-return valve (152), and pumping means (110) operable to pump fluid from the chamber.

20 Claims, 8 Drawing Sheets

PUMPS

CROSS-REFERENCE TO RELATED APPLICATIONS

This application is a 371 National Stage Application of International Application No. PCT/GB2011/050848 filed Apr. 28, 2011, and which claims priority to United Kingdom Application No. 1007292.4 filed on Apr. 30, 2010 and United Kingdom Application No. 1101481.8 filed on Jan. 28, 2011. The contents of the foregoing applications are incorporated herein by reference.

BACKGROUND

The present invention relates to improvements relating to pumps. In particular, the present invention relates to improvements relating to pumps for causing or enhancing an erection of a penis, particularly a human penis.

Erection pumps have been known in the art for some years. The manner in which such pumps work is by placing a chamber over a flaccid penis and evacuating the chamber. The evacuation causes a pressure differential between the inside and outside of the chamber. The lower pressure within the chamber causes blood to flow into the penis and thus make the penis erect.

Many pumps known in the art comprise a chamber having a diaphragm at a lower end thereof and a tube attached at an upper end thereof. The tube is connected to a hand held pump device which is usually in the form of an inflatable bulb having a non-return valve therein. In use, a user places the penis through the diaphragm into the chamber and removes air from the chamber by use of the pump.

WO 2006/024874 discloses a pump that addresses many of the problems of the prior art and provides a device that induces a strong and enduring erection. However, since the evacuated medium envisaged in this prior art document is liquid, not gas, the pressures within the chamber are required to be controllable to a very fine degree to avoid possible health risks.

There still exists, therefore, a desire to improve the functionality and usability of hitherto known pumps.

SUMMARY

It is one aim of embodiments of the present invention to address the above mentioned problems and provide a solution that is easy to use and easy to control, yet which still induces a strong erection which is long lived.

According to a first aspect of the present invention there is provided a pump comprising a chamber adapted to receive a penis, a non-return valve, and pumping means operable to pump fluid from the chamber.

Preferably, the pump comprises a lower portion operable to be arranged proximal to the body of a user, in use, and an upper portion connected to the lower portion, the lower and upper portion being arranged and operable to allow relative rotation there between.

Preferably, the lower portion comprises the pumping means. Preferably, the upper portion comprises the chamber adapted to receive a penis. Preferably, the lower portion comprises a gaiter. Preferably, the upper portion comprises a generally transparent chamber. Preferably, the lower and upper portion are connected to each other at a position toward a lower end of the pump.

Preferably, the pump further comprises rotatable volume adjusting means operable to adjust the volume within the device by rotation.

Preferably, the rotatable volume adjusting means is operable to adjust the volume within the device by rotation thereof relative to the chamber.

Preferably, the rotatable volume adjusting means is situated at or toward an end of the device, preferably an end of the pump arranged to be distal to the body of a user, in use. Preferably, the rotatable volume adjusting device is situated at or toward a head section of the pump. Preferably, the rotatable volume adjusting device is operable to be adjustable between a plurality of discrete positions.

The rotatable volume adjusting means may comprise a rotatable section and a stationary section, preferably being arranged and operable for relative rotation, in use. Preferably, a face of the rotatable section is arranged to oppose a face of the stationary section. Either of the rotatable section or the body section may comprise a plurality of discrete members arranged and operable to engage with a portion of the other of the rotatable member and the stationary member, in use. The plurality of discrete members may be of differing heights. One of the rotatable section or the stationary section may comprise a wave spring. The rotatable portion and the stationary portion may be urged together by a resilient bias. Preferably, one of the rotatable member and the stationary member comprises an undulating face. Preferably, relative rotation of the rotatable member and the stationary member causes the two members to move relative to each other in a direction generally perpendicular to the axis of rotation of the rotatable section. In one embodiment, the rotatable volume adjusting means may be adjustable to a maximum point, to achieve a full lock position.

Preferably, the pump further comprises secondary pumping means at or toward an end of the pump operable to be arranged distal to a user, in use.

Preferably, the secondary pumping means comprises a body and a resilient bias. The secondary pumping means may be housed with the non-return valve. Preferably, the secondary pumping means may be operable, in use, to eject very small amounts of fluid from the chamber. The secondary pumping means may be operable to eject less that 1 cm$^3$ of fluid in a single operation thereof.

The pump may comprise override means to allow a user to prevent fluid escaping form the chamber, preferably by depressing an override button. This is particularly advantageous where the device is sued with liquid.

Preferably, the chamber is adapted to receive a human penis.

Preferably, the chamber is substantially circular in section. Preferably, the chamber is transparent.

Preferably, the chamber comprises a neck section toward a second end thereof, which preferably comprises an outlet.

Preferably, the pump comprises a cap section within which is preferably accommodated the non-return valve. Preferably, the cap section is adapted to fit over the neck section and form a fluid tight seal therewith. Preferably, the secondary pumping means is housed in the cap section.

Preferably, the pump is a penis pump. By penis pump it is meant a pump adapted to cause or enhance an erection to a human penis.

By non-return valve it is meant a valve which allows fluid to travel through the valve in one direction, but not in the other. Preferably, the non return valve is adapted to allow the expulsion of fluid from the chamber, but not the ingress of fluid into the chamber.

The non-return valve may comprise a pressure release button which, upon depression thereof, allows equalisation of the pressure within the chamber and the pressure outside the chamber.

An exterior portion of the neck section may be threaded. An interior portion of the cap section may be threaded. Preferably, the threaded portion of the neck section is adapted to threadedly engage with the threaded portion of the cap section. Preferably, sealing means are provided between the cap section and the neck section which sealing means is preferably an O-ring.

The cap section may be adapted to be screwed onto the neck section.

Alternatively, the cap section may be integrally formed with the chamber.

Preferably, the pumping means is situated toward a first end of the chamber. Preferably, the pumping means is manually actuated. Preferably, the pumping means extends from a first end of the chamber. Preferably, the pumping means is coaxial with the chamber. Preferably, the pumping means comprises a compressible gaiter. Preferably, the pumping means comprises a resilient bias operable to return the pumping means to an uncompressed configuration. Preferably, the pumping means comprises alignment means, which serve to allow correct alignment of the pump with respect to the body of a user.

The pump may comprise means to allow it to attach to a strap. The strap, in use, may extend over a user's neck to thereby support the device. This is particularly useful if the pump is used in the shower.

Preferably, the pump comprises sealing means operable to seal the pump onto the body of a user. Preferably, the sealing means is situated at the first end of the pump. Preferably, the sealing means comprises a sealing ring which is preferably made from closed cell rubber sponge or similar.

Preferably, the sealing means comprises a cutaway section on a face thereof which seals against the body of a user, when in use. Preferably, the sealing means comprises a ring having a cutaway section therefrom.

Preferably, the sealing means comprises a sealing ring having a chamfer along a section of an underside thereof.

Preferably, the pumping means further comprises an internal membrane. Preferably, the internal membrane is arranged and operable to provide a substantially smooth surface within the pump.

In one embodiment, the pumping means may further comprise a gas filled chamber which is preferably annular in shape. Preferably, the gas filled chamber is attached to an inner face of the sealing ring. Preferably, the gas filled chamber is operable to be compressed by the application of pressure by a user. Preferably, a spring return force of the gas filled chamber is greater than the resilient bias of the gaiter.

Preferably, between the gaiter and the hollow chamber is a fixing ring. Preferably, the fixing ring is formed of polycarbonate. Preferably, the fixing ring is adapted to provide lateral and reciprocal support.

Preferably, the chamber comprises indicia to allow a label to be correctly aligned thereon. The indicia may be in the form of one or more rib upstanding from the body of the chamber. Alternatively or additionally, the indicia may serve to indicate correct alignment of the pump with respect to the body of a user.

The pump may comprise pressure measuring means, which may be a pressure gauge. The pressure gauge is preferably operable to measure the pressure within the chamber and preferably display it to a user, in use. The pump may comprise a socket into which the gauge may be housed, preferably in the chamber of the pump.

According to a second aspect of the present invention there is provided a method of causing or enhancing an erection of a human penis comprising inserting a generally flaccid penis into a chamber of the pump and using pumping means to pump water from the chamber through a non-return valve.

According to a third aspect of the present invention there is provided a pump comprising a chamber adapted to receive a penis, a non-return valve, and pumping means operable to pump fluid from the chamber, characterised in that the pump comprises a lower portion operable to be arranged proximal to the body of a user, in use, and an upper portion connected to the lower portion, the lower and upper portion being arranged and operable to allow relative rotation there between.

According to a fourth aspect of the present invention, there is provided a pump comprising a chamber adapted to receive a penis, a non-return valve, and pumping means operable to pump fluid from the chamber, characterised in that the pump further comprises rotatable volume adjusting means operable to adjust the volume within the device by rotation.

According to a fifth aspect of the present invention, there is provided a pump comprising a chamber adapted to receive a penis, a non-return valve, and pumping means operable to pump fluid from the chamber, characterised in that the pump further comprises secondary pumping means at or toward an end of the pump distal to a user, in use.

According to a sixth aspect of the present invention there is provided a pump comprising a first chamber adapted to receive a penis, a secondary chamber being operable to receive and retain a fluid and being connected to the first chamber via a non-return valve; and pumping means operable to pump fluid from the first chamber to the second chamber.

Advantageously, the provision of a secondary chamber allows a user to expel fluid (such as water) from the first chamber there into, without the need for a user to be in the bath or shower, because the fluid is received and retained in the second chamber. The second chamber may comprise a further non return valve.

The pump described in relation to the above aspects may also comprise secondary pumping means, preferably in the form of a manually actuated pump. The secondary pumping means may be arranged to pull fluid through the non return valve out of the chamber.

The secondary chamber may be part of the secondary pumping means. The secondary pumping means may comprise a ball pump, which ball pump may comprise a non-return valve.

According to a yet further aspect of the present invention there is provided a pump comprising a first chamber adapted to receive a penis, a non-return valve, and pumping means operable to pump fluid from the chamber, wherein the pump further comprises a secondary pump operable to pull fluid through the non-return valve.

The secondary pumping means may be situated at or toward an end of the pump, preferably at or toward an end of the pump distal to the pumping means (being primary pumping means).

The present inventors have also invented an insert for use in a pump according to the present invention or for use in prior art pumps. The insert provides the means to adjust enhanced stimulation for a user by means of negative pressure allowing him to achieve an erection more quickly or to use the device as a hydro/air stimulation device.

Therefore, according to an alternative aspect of the present invention, there is provided an insert for a pump, the insert comprising an internal cavity, an aperture opening into the internal cavity and locating means operable to locate the insert in the pump.

The insert preferably comprises a fluid impermeable membrane.

Preferably, the locating means comprises a circumferential rib.

Preferably, the locating means are operable to locate and retain the insert in the pump.

According to a further aspect of the present invention there is provided a pump and insert assembly; the pump comprising a chamber adapted to receive a penis, a non-return valve, and pumping means operable to pump fluid from the chamber; the assembly further comprising an insert arranged substantially inside the chamber and being located in the pump by locating means, the insert comprising an internal cavity and an aperture opening into the internal cavity.

The invention also extends to a kit comprising a pump as described above and an insert.

All of the above aspects may be combined with any feature described herein and in any combination.

BRIEF DESCRIPTION OF THE DRAWINGS

For a better understanding of the invention, and to show how embodiments of the same may be carried into effect, reference will now be made, by way of example, to the accompanying diagrammatic drawings in which.

DETAILED DESCRIPTION

Figure 1:
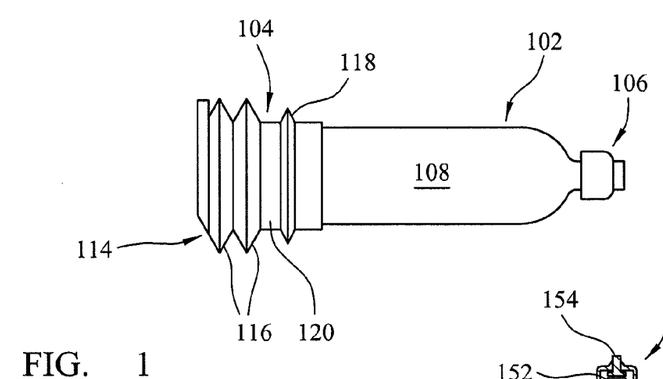
FIG. 1 shows a schematic view of a pump according to the present invention.

Referring firstly to FIG. 1 there is shown a pump 102 having a cylindrical chamber 108 which is generally hollow, a base section 104 at a first end thereof and a head section 106 at a second end thereof.

Figure 5:
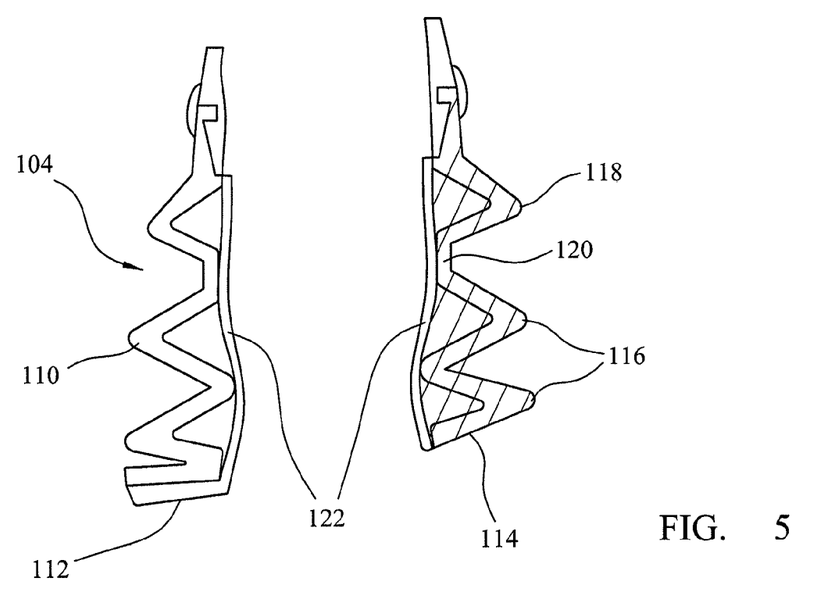
FIG. 5 shows a sectional view of a compression gator of the pump.

The base section 104 is shown enlarged in FIG. 5 and comprises a rubber gaiter 110 which connects at an upper end thereof to the cylindrical chamber 108. The connection between the gaiter 110 and the chamber 108 allows relative rotation there between, thus enabling the lower portion of the pump to be rotated while the chamber is static. This allows a user to rotate the gaiter 110 in use, thus allowing easy movement between different pump orientations. This is particularly advantageous when the pump is being used as an aid to erectile dysfunction, especially in conjunction with a constriction ring (not shown).

At a lower end of the rubber gaiter 110 there is attached a sealing ring 112 which is formed from closed cell rubber sponge. The sealing ring 112 has a chamfer 114 at one side thereof thus allowing the sealing ring to accommodate the testicles of a user in one arrangement, or to be arranged in an acute angle to the body of a user in an alternative arrangement that will be discussed in further detail hereunder.

The gaiter 110 comprises two major compression rings 116 toward a lower end thereof and a single minor compression ring 118 toward an upper end thereof. The major and minor compression rings 116, 118 are separated by a spacer 120. The compression rings have acute angles of about 80°, thus better resistive forces are achieved. Furthermore, on an inner side of the gaiter 110 is an elastically deformable liner 122. The liner 122 serves to provide a smooth inner surface inside the gaiter 110 thus reducing the likelihood of the gaiter 110 chafing a user, in use and also offering hygienic benefits to the pump 102. As will be appreciated with reference to the accompanying drawings, the further embodiment of the pump shown in FIG. 7 does not comprise a spacer 120.

In use, the gaiter 110 may be compressed in a concertina type action, thus decreasing the volume inside the pump. The gaiter 110 has spring properties which restore its compressed state back to its uncompressed state. Accordingly, compression of the gaiter 110 causes fluid to be expelled from the chamber (vie the non return valve assemblies, as discussed hereunder).

Figure 2:
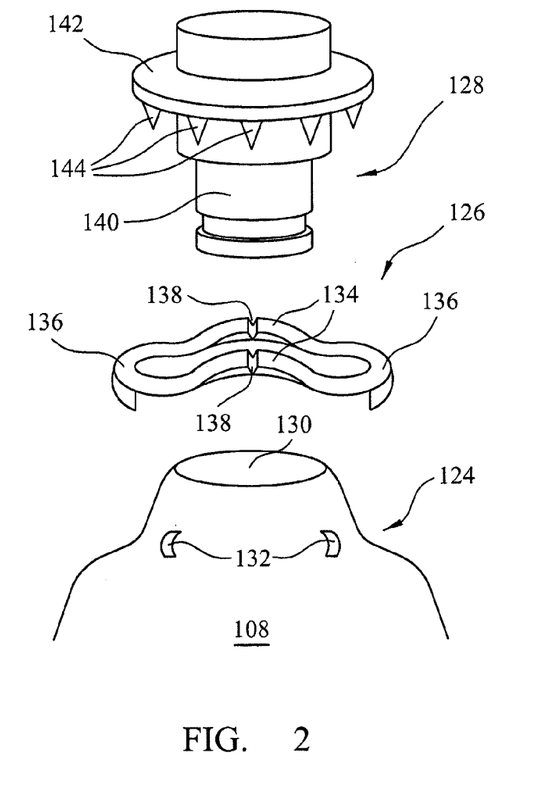
FIG. 2 shows a schematic exploded view of a portion of the head section of a pump.

Referring now to FIG. 2 there is shown an exploded view of an exploded view of a part of the head section 106 of the pump 102. As can be seen in FIG. 2, this part of the head section 106 has three components being an upper part 124 of the chamber 108, a wave spring 126 and a rotatable member 128. The upper part 124 of the chamber 108 comprises a circular aperture 130 opening into the body of the chamber 108. Through the aperture 130 toward the top of the chamber is situated a pair of shoulders 132 diametrically opposed to each other. The shoulders 132 serve to locate and retain the wave spring 126 as will be described hereunder.

The wave spring 126 is generally circular in plan, but has an undulating profile as is shown in FIG. 2 such that it has two diametrically opposed high points 134, and two diametrically opposed low points 136. The low points 136 serve to locate on the shoulders 132 of the chamber 108 as described above. At each of the two high points 134 there is a detent 138 that extends the width of the spring 126. The detents 138 are operable in use to accommodate spikes of the rotatable member 128 as will be described hereunder.

The rotatable member 128 as shown in FIG. 2 comprises a generally cylindrical body 140 having a circumferential platform 142 extending radially outward therefrom and generally encircling the body 140. Extending downward from the platform 142 at discrete positions there around are a number of spikes 144 having differing heights.

When the rotatable member 128 is assembled along with the wave spring 126 inside the upper part 124 of the chamber 108, rotation of the rotatable member 128 causes the spikes of differing height to travel around the wave spring 126, thus adjusting the height of the rotatable member 128 above shoulders 132 of the chamber 108. Furthermore, the detents 138 allow different spikes locate therein thereby allowing different discrete positions of rotation of the rotatable member to be achieved. In use, therefore, when the chamber is under low pressure (partial vacuum, for example), the extent of the low pressure can be minutely and discretely varied by rotation of the rotatable member 128.

Figure 3:
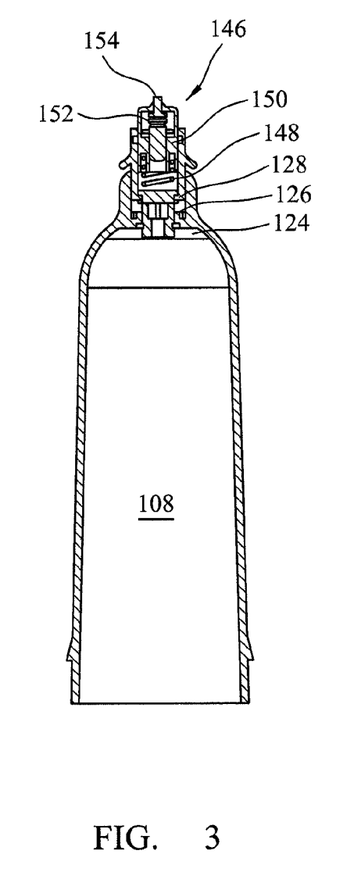
FIG. 3 shows a sectional view of an upper section of the pump.
Figure 4:
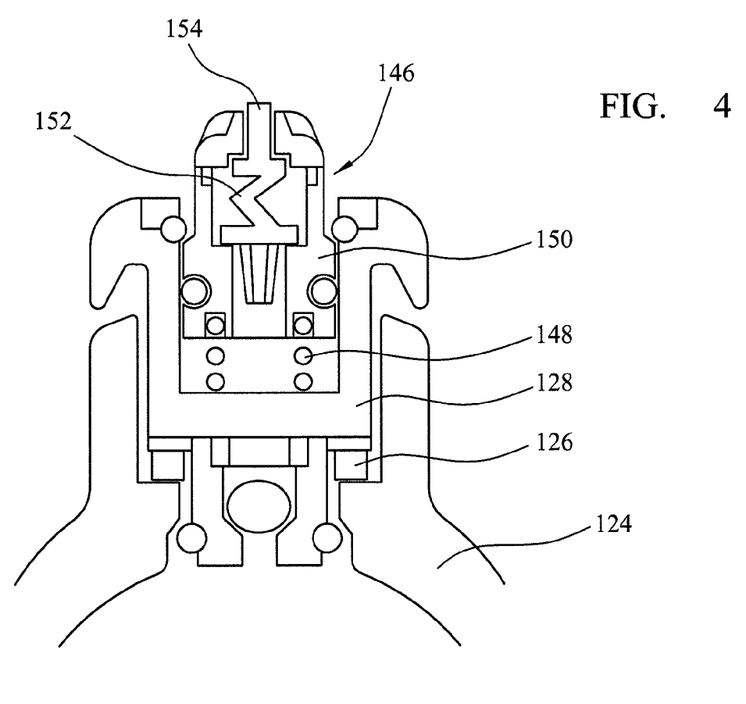
FIG. 4 shows a sectional view of a cap section of the pump.

Referring now to FIGS. 3 and 4 there is shown a sectional view of the head section of the pump 106. It should be noted that the head section shown in FIGS. 3 and 4 shows the assembled wave spring 126 and rotatable member 128 discussed above. Also shown in FIGS. 3 and 4 is a further way of altering the pressure within the chamber 108 in the form of a further pump 146 arranged centrally in the housing of the rotatable member 128.

The further pump 146 comprises a spring 148 and a body 150. Centrally arranged within the body 150 is a non-return valve 152. The spring 148 is arranged to bias the body 150 away from the chamber 108, thus depressing the body 150 against the spring 148 causes fluid to be expelled from the chamber 108 out of the non-return valve and the body 150 to be pushed back away from the chamber 108 by the spring 148, thereby reducing the pressure in the chamber in a very small incremental manner.

The non return valve 152 also comprises a safety button 128 which, by depressing, when not in a locked position allows fluid outside the chamber to re-enter the chamber, thereby equalising the pressure and reducing the partial vacuum. At the top of the valve assembly is a valve manual close button 154 for use when the device is inverted, for example when being filled in the shower.

Figure 6:
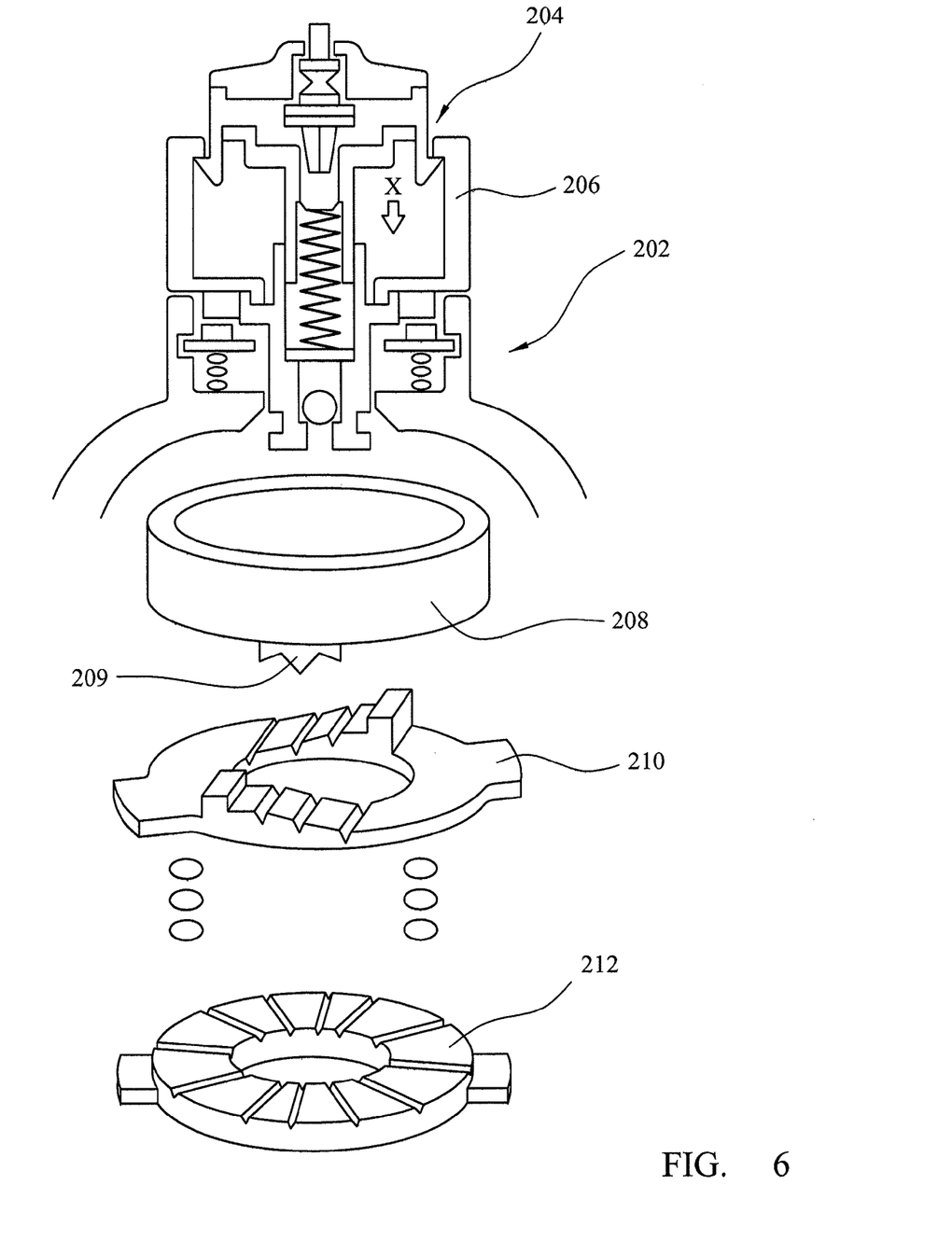
FIG. 6 shows a sectional view of a second embodiment of a cap section of the pump.

Referring now to FIG. 6 there is shown a second embodiment of a cap section 202 of the pump. The cap section 202 is largely similar to that discussed above in relation to FIG. 4. However, the pressure release at the head works in a slightly different way. An insert 204 is depressed down into the body 206 to equalize pressure, in use.

Further differences in this embodiment exist in the way the volume adjustment means operates. Instead of having a wave spring to cause the volume to adjust, this embodiment provides a collar 208 having a downwardly extending projection 209. Beneath the collar 208 may be situated either of the annular stationary members 210 and 212 shown in FIG. 6. The first annular member 210 has a number of discrete steps. Accordingly, rotating the cap section (thus also the collar), causes the cap section 202 to rise and fall with respect to the annular member (and therefore the chamber). The second annular member 212 is similar but has an undulating upper face with a number of small detents therein. Accordingly, in a similar manner to that described above, rotation of the cap causes the cap to rise and fall with respect to the chamber. In this manner, the pressure within the chamber can be minutely controlled by a user. Less resistance on the spring the more it will open under increased negative pressure.

In order to use the pump to produce an erection to a human penis, the pump 102 and a user may be immersed in liquid, such as in a bath, hot tub or jacuzzi. Alternatively, the device may be used in air. In one arrangement, the device may be filled with liquid, such as in a shower scenario, but the user not necessarily immersed in liquid The flaccid or semi erect penis is then placed into the chamber 108 via the base section 104. The sealing ring 112 is pulled down so that it abuts the user's pubic area and forms a seal. The chamfer 114 is arranged either against the testicular region to provide safety and comfort, or the chamfer 114 may be arranged at the pubic region of the user and the device arranged at an acute angle to the body of the user. The user then pulls the pump toward the body thus causing the gaiter 110 to compress. Fluid within the chamber is thereby expelled through the non-return valve 152 of the head section 106, because the volume of the chamber 108 is decreased. The spring return force of the gaiter 110 attempts to restore the pump to its original internal volume and thereby reduces the pressure inside the chamber 108. Continuing the use, the gaiter 110 may be compressed again to expel more fluid through the non-return valve 152 of the head section 106. The penis is thereby encouraged to expand (by the ingress of blood) in order to return the gaiter 110 to its uncompressed state.

Once a reasonable vacuum has been achieved, the user can perform small incremental adjustments of the pressure within the device as follows.

Firstly, by rotating the rotatable member 128, the head section 106 is pulled away from the chamber 108, thereby decreasing the pressure within the chamber. Furthermore, the detents 138 allow a user to alter the pressure incrementally to different discrete levels by the spikes 144 of differing heights locating in the detents 138. Less tension on the spring the less negative pressure it will hold. This also operates as a safety feature to prevent excessive negative pressure generated by a user because if a user induces a lower tension than that of the spring, the spring deflects to allow pressure to leak out.

Alternatively or additionally, a user may perform small adjustments to the vacuum within the chamber by using the pump 146 to expel further tiny amounts of fluid.

When the penis is fully erect (after perhaps 20 minutes) the pressure on the penis may be released by twisting the cap section 146 from the neck section 134 thereby breaking the seal of the O-ring.

A user may release the pressure within the chamber by manually operating the pressure release button 128 thus allowing the ingress of fluid into the chamber 108. This serves as an added safety feature of the pump 102.

A pump made in accordance with the present invention has many advantages over prior art pumps. For example, the chamber 108 is rotatable with regard to the gaiter 104, thereby allowing easier manipulation of the device in use. Furthermore, the device 102 comprises two different ways of providing small incremental pressure changes within the chamber 108, thus providing a device that is much more sensitively adjusted, thus proving a safer device that is easier to use.

Figure 7:
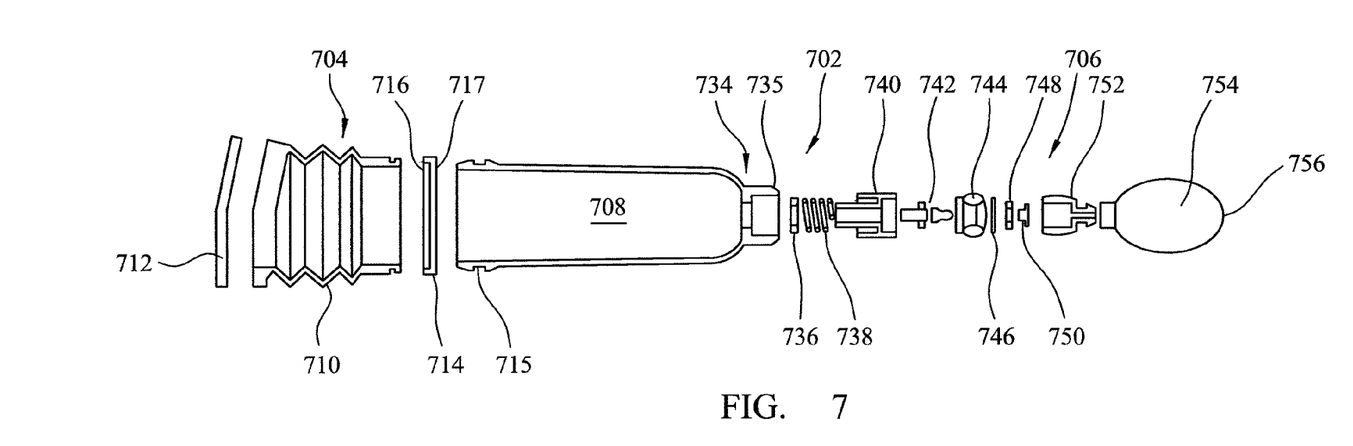
FIG. 7 shows an exploded sectional view of a pump according to the present invention.

Referring now to FIG. 7 there is shown a pump 702 having a cylindrical chamber 708 which is generally hollow, a base section 704 at a first end thereof and a head section 706 at a second end thereof.

The base section comprises a compressible rubber gaiter 710 which connects at an upper end thereof to an exterior face 716 of a fixing ring 714 which is formed of polycarbonate. The fixing ring 714 is located in a circumferential recess 715 on the outer walls of the chamber 708 to allows easy manufacture.

At a lower end of the rubber gaiter 710 there is attached a sealing ring 112 which is formed from closed cell rubber sponge.

In use, the gaiter may be compressed in a concertina type action, thus decreasing the volume inside the pump. The gaiter 710 has spring properties which restore its compressed state back to it uncompressed state.

The hollow chamber 708 narrows toward a second end thereof to a neck section 734. The neck section 734 is circular in cross section and has moulded therein a housing 735 for a valve. The neck section 734 is substantially concentric with the hollow chamber 708.

Constituent parts of the valve mechanism are also shown exploded in FIG. 7. Working from the base of the valve up (or from left to right in FIG. 7), the valve mechanism comprises an O ring 736 which locates at a base of the housing 735, in use. Above the O ring 736 is a spring 738, which sites beneath the valve assembly, thereby biasing the assembly outward (ie. away from the chamber 708). The valve assembly comprises a valve body 740, which houses a valve 742, having a valve top 744 situated thereabove.

In use, the valve assembly works as a non-return valve, allowing fluid to be expelled form the chamber 708, but not back into the chamber 708.

Furthermore, the underside of the valve body 740 and an upper side of the housing 735 comprise circumferential ramped protrusions, which coincide with each other and allow a user to twist the valve body to thereby allow the non-return valve body 740 to be locked such that application of pressure to the valve mechanism does not release pressure in the chamber.

Above the valve top 744 is an o-ring seal 746, above which is a sealing washer 748 and a membrane sealing washer 750.

Situated on top of the valve assembly described above is a pump connector 752 and a manual ball pump 754. The manual ball pump 754 comprises a compressible chamber and a non-return valve 756 situated at an end distal to the chamber 708.

In order to use the pump to produce an erection to a human penis, a flaccid or semi erect penis is placed into the hollow chamber 708 via the base section 704. The sealing ring 712 is pulled down so that it abuts the user's pubic area and forms a seal. The user then pulls the pump toward the body thus causing the gaiter 710 to compress. Fluid within the chamber is thereby expelled through the non-return valve of the head section 706, because the volume of the chamber 708 is decreased. The spring return force of the gaiter 710 attempts to restore the pump to its original internal volume and thereby reduces the pressure inside the chamber 708. The gaiter 710 is once more compressed to expel more liquid through the non-return valve of the head section 706. The penis is thereby forced to expand (by the ingress of blood) under vacuum.

The pump may be arranged so that the chamfer allows an area for the testicles, thereby reducing pressure on this area. In an alternative arrangement, the pump may be rotated through 180°, an the chamfered area pulled to the body of a user above the penis and the pump being angled upwards. In this arrangement the device may be used in the shower, for example.

Once a suitable pressure is achieved, the pressure in the device may be locked off by twisting the valve body 740, then adding the ball pump 754 to the end of the device. This device allows a user to make fine adjustments to the pressure of the device and also to retain any fluids therein that are expelled from the device (since the device may be filled with water). This works by squeezing the ball pump, thereby expelling fluid therefrom (which may be air) via the non return valve 756. In turn, the now low pressure in the ball pump 754 pulls fluid through the non-return valve 742 to further reduce the pressure in the chamber 708. Also, because the system now comprises two chambers having equilibrating pressures, any increase of pressure from the first chamber is restored by the low pressure in the secondary chamber.

This arrangement also allows a user to simply fill the device with fluid (such as water, for example), arrange over the penis and use the device while not generally immersed in water. This is of particular use to people in wheelchairs.

When the penis is fully erect the pressure on the penis may be released by twisting the valve 740 and depressing the valve assembly, thereby breaking the seal of the O-ring 736

Figure 8:
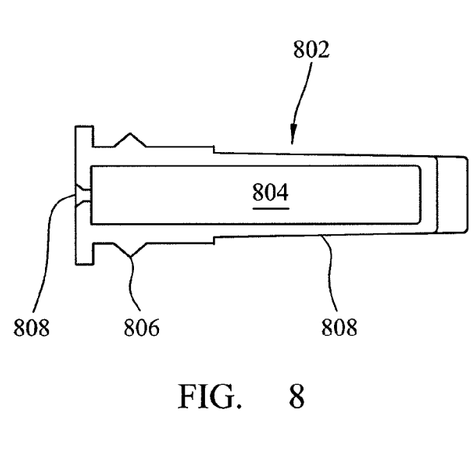
FIG. 8 shows a sectional view of an insert for a pump.

Referring to FIG. 8 there is shown an insert 802 for a pump according to the invention or according to prior art pumps. The insert is generally cylindrical and comprises an internal cavity 804 and locating means 806 in the form of a circumferential rib, sized and operable to fit within a circumferential ring of the gaiter of a pump. The insert 802 comprises an aperture 808 at an end thereof to allow access into the internal cavity 804. The wall of the cavity 809 is made from a fluid impermeable material.

Figure 9:
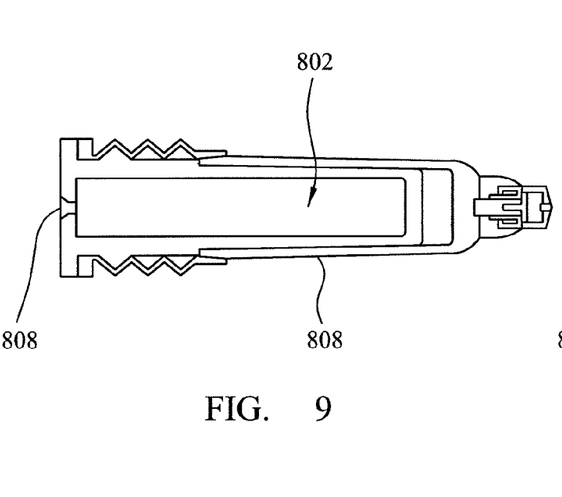
FIG. 9 shows a sectional view of the insert arranged within a pump.
Figure 10:
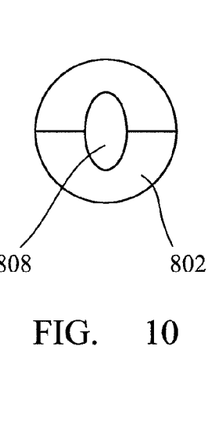
FIG. 10 shows an end view of the insert.

FIG. 9 shows the insert 802 located in a pump according to the present invention, while FIG. 10 shows an end view of the insert 802 showing the aperture 808.

FIGS. 11 to 14 show a second embodiment of an insert 902 in a first unexpanded configuration, whereas FIGS. 15 to 18 show the second embodiment of the insert 902 in a second, expanded configuration, as will be explained below. The second embodiment is substantially the same as the first embodiment and like features are numbered similarly, except that they start with a numeral 9 rather than 8.

Figure 11:
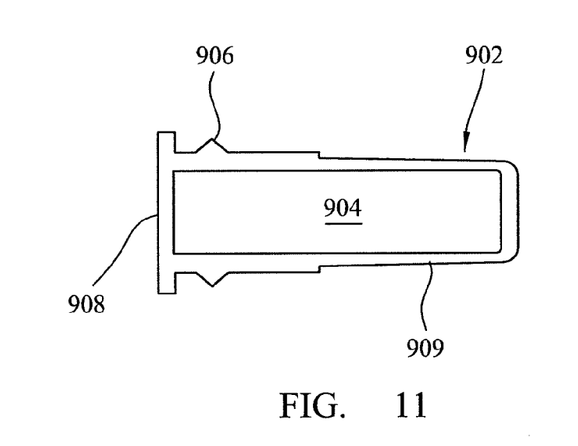
FIG. 11 shows a sectional view of second embodiment of an insert in a first configuration.

In use, the insert 802, 902 is inserted into a pump and located via locating means 806, 906. This can give the user 2 options of use, one is a sex simulator/stimulator, the second is as an hydro air combination pump.

Figure 12:
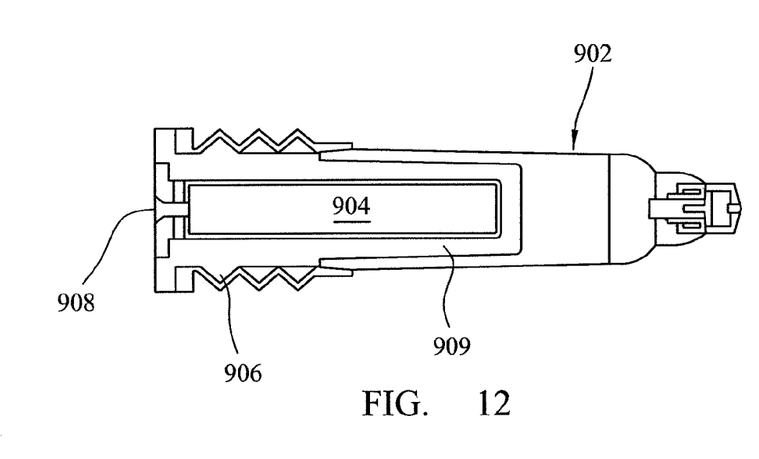
FIG. 12 shows a sectional view of the second embodiment of the insert in a first configuration arranged in a pump.
Figure 13:
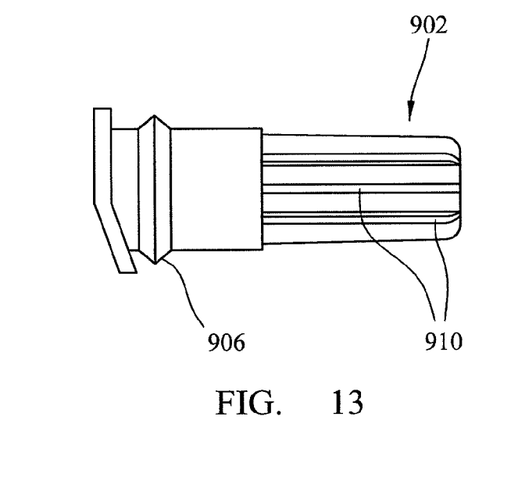
FIG. 13 shows a perspective view of the second embodiment of the insert in a first configuration.
Figure 14:
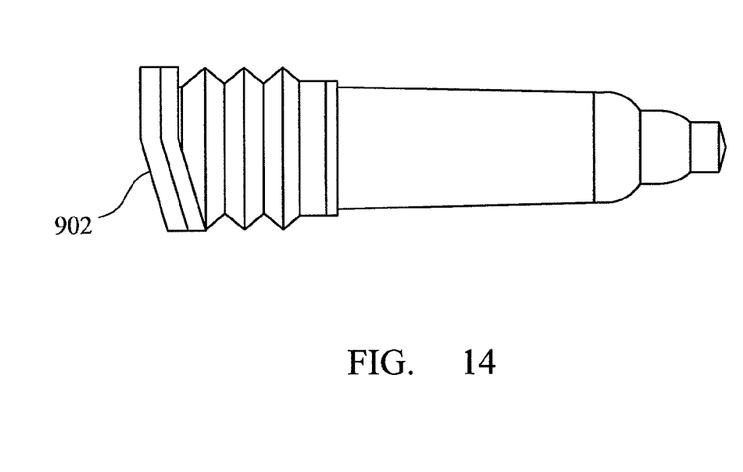
FIG. 14 shows a perspective view of the second embodiment of the insert in a first configuration arranged in a pump.
Figure 15:
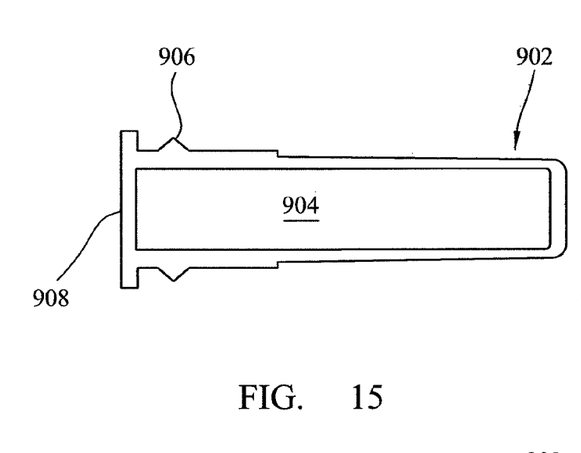
FIG. 15 shows a sectional view of the second embodiment of an insert in a second, expanded, configuration.
Figure 16:
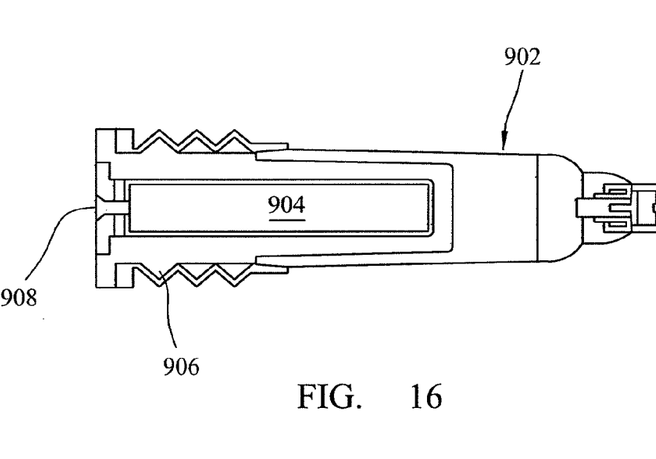
FIG. 16 shows a sectional view of the second embodiment of the insert in a second, expanded, configuration arranged in a pump.
Figure 17:
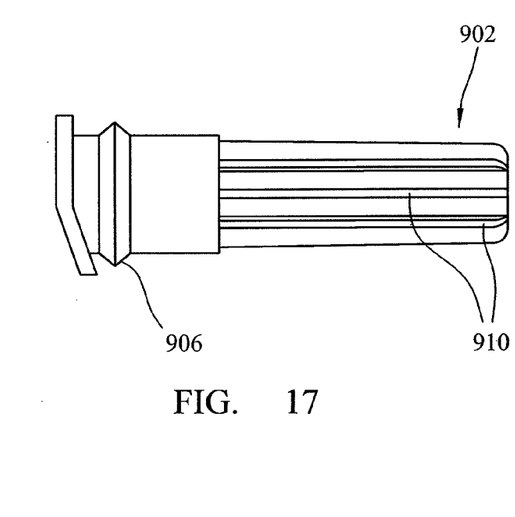
FIG. 17 shows a perspective view of the second embodiment of the insert in a second, expanded, configuration.
Figure 18:
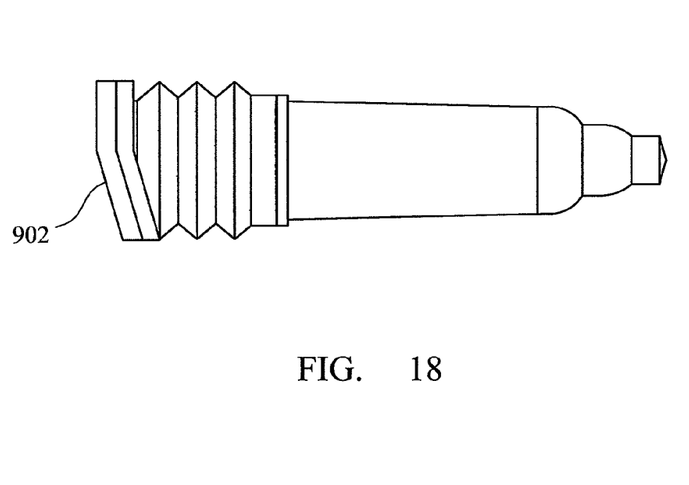
FIG. 18 shows a perspective view of the second embodiment of the insert in a second, expanded, configuration arranged in a pump.

In the first use as a sex simulator/stimulator. warm water may be included to allow the insert to be heated to give true sexual feeling for the user). In this use, the user inverts the pump 702, depresses the valve 742 and part fills the chamber 708 with warm water. The insert 802, 902 is the inserted and located in the pump as shown in FIG. 12 and negative pressure induced between the outer wall of the chamber 708 and the wall of the cavity 809/909 by means of compressing either gaiter 710 or attaching hand ball pump 754. The valve 742 is then locked off by latching in to place. if the device is then turn up right so the air within can be expelled this will make the water line the full area between the wall of the cavity and the outside of the chamber 708. This will hold the negative pressure inside the chamber 708 and not allow water out of the chamber. The penis can now be inserted and sexual simulation undertaken, the hot water providing a feeling of realism. Drawing the penis in and out of the insert in slow strokes will give sexual stimulation. If the user wants to change the tension or resistance reduce or increase the negative pressure within the chamber 708 increase vacuum by unlatching 742 and attaching 754 to decrease vacuum twist 740 and depress, this will change the size of 802.

As discussed above and as shown in FIGS. 15 to 18, the decrease in pressure causes the insert to change shape—stretch and expand under negative pressure.

In an alternate mode of use, "hydro/air" combination—the insert 802, 902 is inserted into chamber 708. Depending on internal size requirement apply the hand pump 754 may be employed to create partial vacuum or compress 710. The pump and insert assembly is then inverted and fluid preferably water is inserted (which cushions the penis in water without ever expelling water from the chamber 708). Next the penis is inserted and the assembly pulled down and sealed against the user's pelvis against ring 712. The water is held inside the sealed insert chamber which can expand but does not release water which provides induced negative pressure. This mode of operation has all of the benefits of using water and can be used out of the water environment. Once the insert has reached it full size no more pressure will be able to be removed from within the chamber 708. This can have a benefit to first time users and those recovering from medical conditions such as abdominal surgery. Where the device has to be removed and reapplied for the user to re-adjust and gain an increase in negative pressure. This removal also forces the flushing action of blood in and out of the users penis which in turn can remove toxins that are the underlying cause of erection problems in later life.

Figure 19:
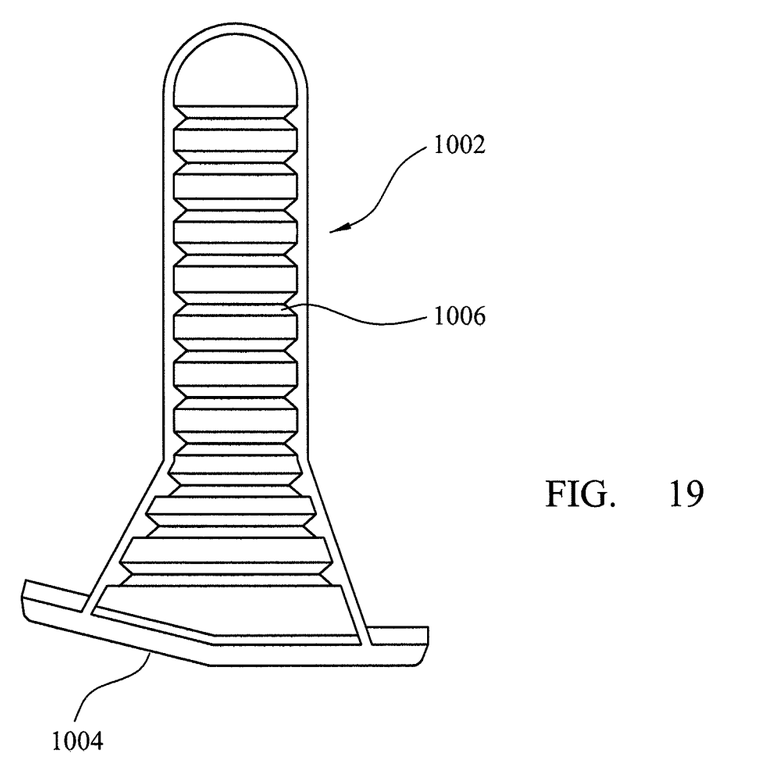
FIG. 19 shows a third embodiment of an insert.

Referring now to FIG. 19 there is shown a further embodiment of an insert 1002. The insert 1002 has a chamfered base 1004 to match the base of the pump (not shown) and a ribbed interior surface 1006.

Figure 20:
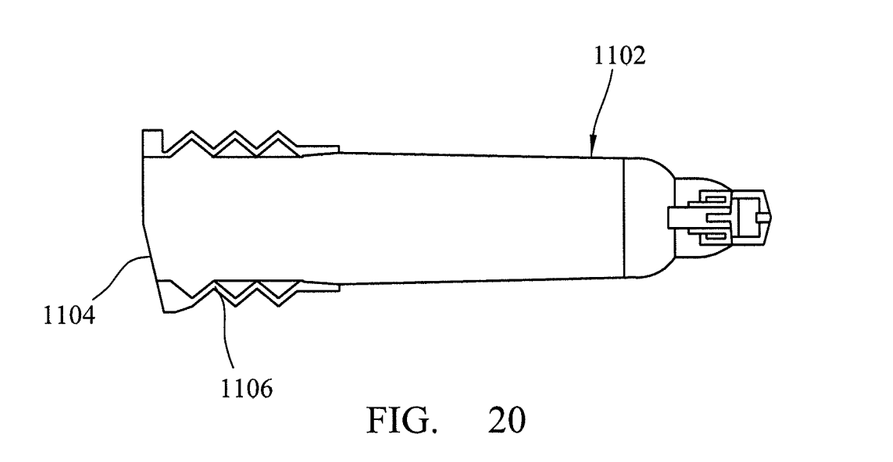
FIG. 20 shows a cross sectional view of a pump.

FIG. 20 shows a further embodiment of a pump 1102 having an internal membrane 1104 to cover the gaiter 1106, in a similar manner to that shown in FIG. 5.

Figure 21:
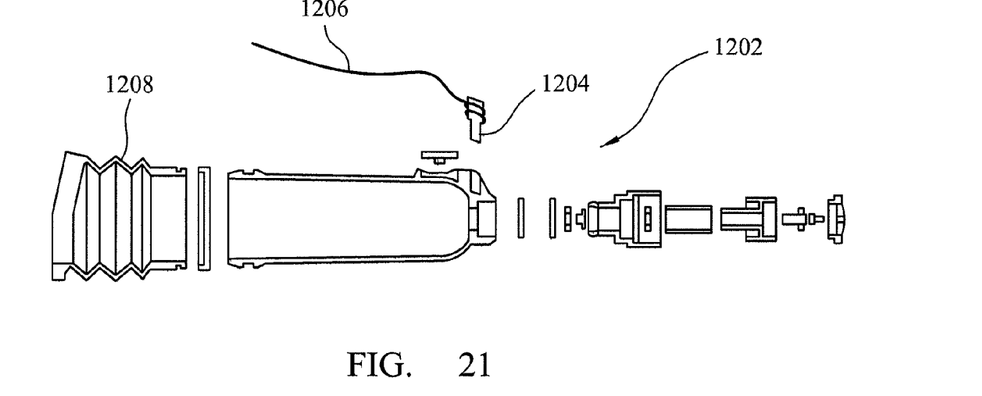
FIG. 21 shows an exploded view of a pump according to the invention.

FIG. 21 shows an exploded view of a pump 1202 having attachment means 1204 to allow a strap 1206 to be attached to the pump 1202 and having a valve mechanism similar to that described in relation FIG. 6. The pump 1202 has a gaiter 1208 having a reduced size of convolutes to provide a more dynamic device.

Figure 22A:
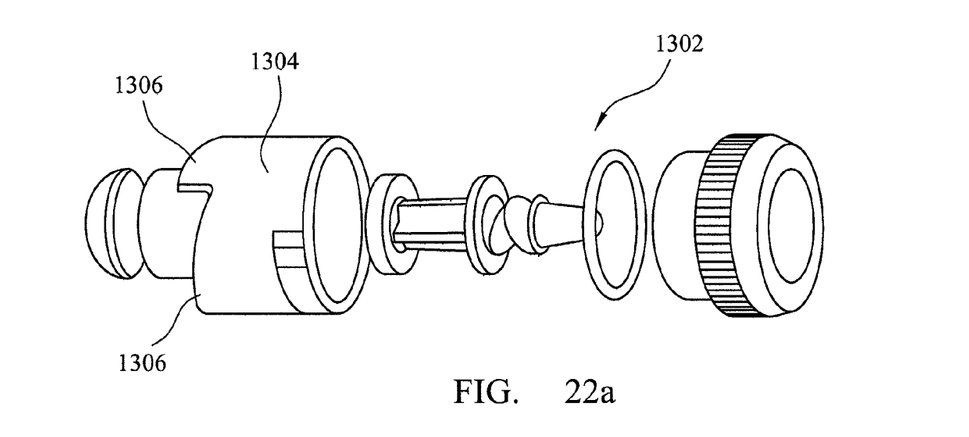
FIG. 22a shows an exploded view of a valve assembly.
Figure 22B:
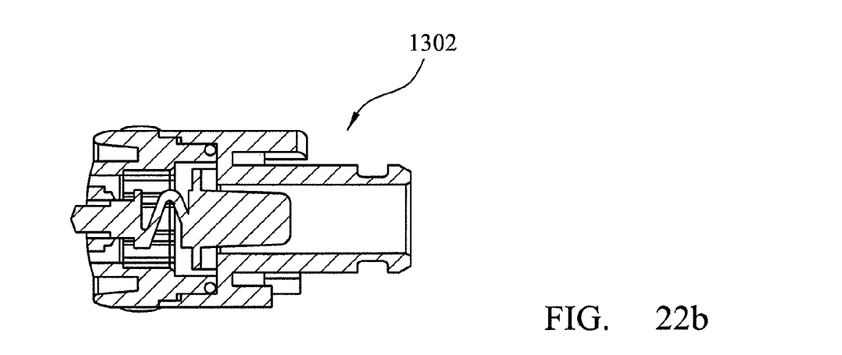
FIG. 22b shows a cross sectional view of the valve of FIG. 22.

FIG. 22*a* and FIG. 22*b* show a valve mechanism 1302 for use in a pump of the present invention. The valve 1302 comprises a barrel 1304 having a series of ramps 1306 on an underside thereof to thereby allow the valve to alter the volume within the the pump by twisting the valve 1302, in a similar manner to that described above in relation to FIG. 6.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A pump comprising:
   a chamber adapted to receive a penis;
   a non-return valve; and
   pumping means operable to pump fluid from the chamber, wherein the pumping means comprises a compressible gaiter, wherein the pumping means further comprises an internal membrane that is secured over an inner side of the gaiter and is operable to provide a substantially smooth surface inside the gaiter.

2. A pump according to claim 1, wherein the pump comprises a lower portion operable to be arranged proximal to a body of a user, in use, and an upper portion connected to the lower portion.

3. A pump according to claim 1, wherein the pump further comprises rotatable volume adjusting means operable to adjust volume within the pump by rotation.

4. A pump according to claim 3, wherein the rotatable volume adjusting means is operable to adjust the volume within the pump by rotation thereof relative to the chamber.

5. A pump according to claim 3, wherein the rotatable volume adjusting means is situated at or toward an end of the pump.

6. A pump according to claim 5, wherein the rotatable volume adjusting means is situated at or toward an end of the pump arranged to be distal to a body of a user, in use.

7. A pump according to claim 3, wherein the rotatable volume adjusting means comprises a rotatable section and a stationary section that are arranged and operable for relative rotation, in use.

8. A pump according to claim 7, wherein relative rotation of the rotatable section and the stationary section causes the two sections to move relative to each other in a direction generally perpendicular to an axis of rotation of the rotatable section.

9. A pump according to claim 1, which further comprises secondary pumping means at or toward an end of the pump operable to be arranged distal to a user, in use.

10. A pump according to claim 9, wherein the secondary pumping means comprises a body that is resiliently biased.

11. A pump according to claim 9, wherein the secondary pumping means is operable, in use, to eject very small amounts of fluid from the chamber.

12. A pump according to claim 1, which further comprises means to allow the pump to attach to a strap.

13. A pump according to claim 1 which further comprises a cap section within which is accommodated the non-return valve, the non-return valve comprising a pressure release button which, upon depression thereof, allows equalisation of pressure within the chamber and pressure outside the chamber.

14. A pump according to claim 1, wherein the pumping means is situated toward a first end of the chamber and is manually actuated.

15. A pump according to claim 1, which further comprises sealing means operable to seal the pump onto a body of a user.

16. A pump according to claim 15, wherein the sealing means comprises a sealing ring.

17. A pump according to claim 16, wherein the sealing ring is made from closed cell rubber sponge.

18. A pump comprising a chamber adapted to receive a penis, a non-return valve, and pumping means operable to pump fluid from the chamber, wherein the pump further comprises rotatable volume adjusting means operable to adjust volume within the pump by rotation, and the rotatable volume adjusting means is operable to be adjustable between a plurality of discrete positions.

19. A pump comprising a chamber adapted to receive a penis, a non-return valve, and pumping means operable to pump fluid from the chamber, further comprising override means to allow a user to prevent fluid escaping from the chamber, by depressing an override button.

20. A method of causing or enhancing an erection of a human penis comprising inserting a generally flaccid penis into a chamber of a pump according to claim 1 and using pumping means to pump fluid from the chamber through the non-return valve.

* * * * *